United States Patent
Ohkuma et al.

(10) Patent No.: US 7,378,560 B2
(45) Date of Patent: May 27, 2008

(54) RUTHENIUM COMPLEX AND PROCESS FOR PRODUCING TERT-ALKYL ALCOHOL THEREWITH

(75) Inventors: Takeshi Ohkuma, Sapporo (JP); Christian A. Sandoval, Shanghai (CN); Ryoji Noyori, Tokyo (JP)

(73) Assignees: Kanto Kangaku Kabushiki Kaisha, Tokyo (JP); Nagoya Industrial Science Research Institute, Nagoya (JP)

( * ) Notice: Subject to any disclaimer, the term of this patent is extended or adjusted under 35 U.S.C. 154(b) by 0 days.

(21) Appl. No.: 11/665,919

(22) PCT Filed: Oct. 24, 2005

(86) PCT No.: PCT/JP2005/019497

§ 371 (c)(1),
(2), (4) Date: Jun. 21, 2007

(87) PCT Pub. No.: WO2006/046508

PCT Pub. Date: Apr. 5, 2006

(65) Prior Publication Data

US 2007/0265448 A1    Nov. 15, 2007

(30) Foreign Application Priority Data

Oct. 25, 2004    (JP)    .............................. 2004-309919

(51) Int. Cl.
C07C 29/14    (2006.01)
C07F 15/00    (2006.01)
B01J 31/00    (2006.01)

(52) U.S. Cl. .............................. 568/881; 546/2; 546/12; 556/13; 556/18

(58) Field of Classification Search .................... 546/2, 546/12; 556/13, 18; 568/881
See application file for complete search history.

(56) References Cited

FOREIGN PATENT DOCUMENTS

JP    A-11-189600    7/1999
WO    WO 2005/105819 A1    11/2005

OTHER PUBLICATIONS

Christelle Moreau et al.; "Catalytic Asymmetric Hydrosilylation of Ketones Using Mixed-Ligand Ruthenium Complexes;" *Tetrahedron Letters*; vol. 40; pp. 5617-5620; 1999.

*Primary Examiner*—Porfirio Nazario-Gonzalez
(74) *Attorney, Agent, or Firm*—Oliff & Berridge, PLC

(57) ABSTRACT

A tert-alkyl ketone, pinacolone was hydrogenated under pressurized hydrogen in the presence of a ruthenium complex (S)-1 and a base, and corresponding (S)-3,3,-dimethyl-2-butanol was thereby obtained in 100% yield and 97% ee

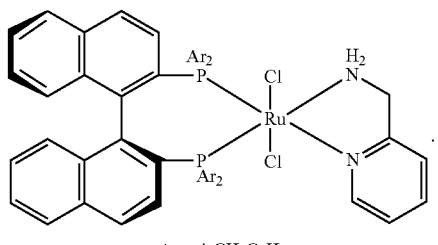

Ar = 4-CH$_3$C$_6$H$_4$
Ruthenium complex (S)-1

7 Claims, No Drawings

RUTHENIUM COMPLEX AND PROCESS FOR PRODUCING TERT-ALKYL ALCOHOL THEREWITH

TECHNICAL FIELD

The present invention relates to a novel ruthenium complex and a process for producing tert-alkyl alcohol therewith.

BACKGROUND ART

Ruthenium complexes $RuX_2$(diphosphine)(1,2-diamine) (wherein X is chlorine, diphosphine is 2,2'-bis-(diphenylphosphino)-1-1'-binaphthyl, and 1,2-diamine is 1,2-diphenylethylenediamine) in the presence or absence of bases rapidly and enantioselectively hydrogenate relatively simple ketones (e.g., acetophenone) in 2-propanol to give corresponding alcohols (e.g., refer to Japanese Unexamined Patent Application Publication No. 11-189600).

DISCLOSURE OF INVENTION

However, hydrogenation reaction of tert-alkyl ketones using the ruthenium complexes mentioned above barely proceeds due to steric factors. Despite the enormous efforts made heretofore, practical techniques for asymmetrical hydrogenation reaction of tert-alkyl ketones have not been found.

The present invention has been made to overcome such a problem and aims to provide a ruthenium complex that can efficiently hydrogenate tert-alkyl ketones. Another object of the present invention is to provide a process for producing a tert-alkyl alcohol, in particular, an optically active tert-alkyl alcohol, by using this ruthenium complex.

The present inventors have made ardent efforts and found a compound represented by general formula (1) to be a ruthenium complex that accelerates hydrogenation reaction of tert-alkyl ketones.

That is, a ruthenium complex of the present invention is represented by:

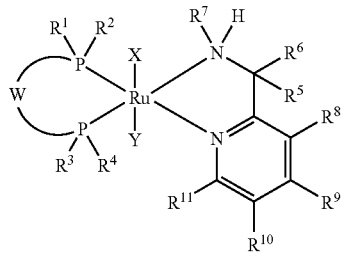

(1)

(wherein W is a substituted or unsubstituted bonding chain; $R^1$ to $R^4$ may be the same or different and each represent a substituted or unsubstituted hydrocarbon group; $R^5$ to $R^{11}$ may be the same or different and each represent hydrogen or a substituted or unsubstituted hydrocarbon group; X and Y represent the same or different anionic groups; and each ligand of Ru may take any configuration).

W in general formula (1) represents a substituted or unsubstituted bonding chain. Examples of such a bonding chain include divalent hydrocarbon chains (e.g., straight-chain hydrocarbons such as $-CH_2-$, $-(CH_2)_2-$, $-(CH_2)_3-$, $-(CH_2)_4-$, and the like, branched-chain hydrocarbons such as $-CH_2CH(CH_3)-$, $-CH(CH_3)CH(CH_3)-$, and the like, and cyclic hydrocarbons such as $-C_6H_4-$, $-C_6H_{10}-$, and the like), divalent binaphthyl, divalent biphenyl, divalent bipyridine, and divalent heterocycles. Among these, a substituted or unsubstituted 1,1'-binaphthyl or 1,1'-biphenyl group having each of 2-position and 2'-position bonded to a phosphine is preferred. These bonding chains may include any of various acceptable substituents such as alkyl, alkenyl, cycloalkyl, aryl, alkoxy, ester, acyloxy, a halogen atom, nitro, and cyano, and the substituents may be bonded to each other via carbon, oxygen, nitrogen, sulfur, or the like. Preferably, W is optically active. For example, when W includes a 1,1'-binaphthyl group, a (R)-1,1'-binaphthyl group or a (S)-1,1'-binaphthyl group is preferred. When W includes a 1,1'-biphenyl group, (R)-1,1'-biphenyl group or a (S)-1,1'-biphenyl group is preferred.

The substituted or unsubstituted hydrocarbon groups represented by $R^1$ to $R^4$ in general formula (1) may be optionally substituted saturated or unsaturated aliphatic or alicyclic hydrocarbon groups, or optionally substituted monocyclic or polycyclic aromatic or aliphatic hydrocarbon groups. For example, they may be selected from hydrocarbon groups such as alkyl, alkenyl, cycloalkyl, cycloalkenyl, phenyl, tolyl, xylyl, naphthyl, phenylalkyl, and the like that may have various acceptable substituents, such as alkyl, alkenyl, cycloalkyl, aryl, alkoxy, ester, acyloxy, a halogen atom, nitro, and cyano. When $R^1$ and $R^2$ form a ring and/or $R^3$ and $R^4$ form a ring, $R^1$ and $R^2$ and/or $R^3$ and $R^4$ may be selected to form a carbon bonding chain on which any of various acceptable substituents such as alkyl, alkenyl, aryl, cycloalkyl, alkoxy, ester, acyloxy, a halogen atom, nitro, and cyano is present. $R^1$ to $R^4$ are preferably phenyl, p-tolyl, m-tolyl, 3,5-xylyl, p-tert-butylphenyl, p-methoxyphenyl, cyclopentyl, and cyclohexyl.

In general formula (1), since a diphosphine derivative $(R^1R^2P-W-PR^3R^4)$, which is a bidentate ligand, coordinates to ruthenium, preferable examples of $R^1$ to $R^4$ and W are described here by giving examples of diphosphine derivatives. Examples of the diphosphine derivatives include BINAP(2,2'-bis(diphenylphosphino)-1-1'-binaphthyl), TolBINAP(2,2'-bis[4-methylphenyl]phosphino]-1,1'-binaphthyl), XylBINAP(2,2'-bis[(3,5-dimethylphenyl)phosphino]-1,1'-binaphthyl), 2,2'-bis[(4-tert-butylphenyl)phosphino]-1,1'-binaphthyl, 2,2'-bis[(4-isopropylphenyl)phosphino]-1,1'-binaphthyl, 2,2'-bis[(naphthalen-1-yl)phosphino]-1,1'-binaphthyl, 2,2'-bis[(naphthalen-2-yl)phosphino]-1,1'-binaphthyl, BICHEMP(2,2'-bis(dicyclohexylphosphino)-6,6'-dimethyl-1,1'-biphenyl), BPPFA(1-[1,2-bis-(diphenylphosphino)ferrocenyl]ethylamine), CHIRAPHOS(2,3-bis(diphenylphosphino)butane), CYCPHOS(1-cyclohexyl-1,2-bis(diphenylphosphino)ethane), DEGPHOS(1-substituted-3,4-bis(diphenylphosphino)pyrrolidine), DIOP(2,3-isopropylidene-2,3-dihydroxy-1,4-bis(diphenylphosphino)butane), SKEWPHOS(2,4-bis(diphenylphosphino)pentane), DuPHOS(substituted-1,2-bis(phospholano)benzene), DIPAMP(1,2-bis[(o-methoxyphenyl)phenylphosphino]ethane), NORPHOS(5,6-bis(diphenylphosphino)-2-norbornene), PROPHOS(1,2-bis(diphenylphosphino)propane), PHANEPHOS(4,12-bis(diphenylphosphino)-[2,2']-paracyclophane), substituted-2,2'-bis(diphenylphosphino)-1,1'-bipyridine, SEGPHOS((4,4'-bi-1,3-benzodioxole)-5,5'-diyl-bis(diphenylphosphine)), BIFAP(2,2'-bis(diphenylphosphanyl)-1,1'-bidibenzofuranyl), BisbenzodioxanPhos([(5,6),(5',6')-bis(1,2-ethylenedioxy)biphenyl-2,2'-diyl]bis(diphenylphosphine), and P-phos(2,2'-6,6'-tetramethoxy-4,4'-bis(diphenylphosphino)-3,3'-bipyridine).

The substituted or unsubstituted hydrocarbon groups represented by $R^5$ to $R^{11}$ in general formula (1) may be optionally substituted saturated or unsaturated aliphatic or alicyclic hydrocarbon groups, or optionally substituted monocyclic or polycyclic aromatic or aliphatic hydrocarbon groups. For example, they may be selected from hydrocarbon groups such as alkyl, alkenyl, cycloalkyl, cycloalkenyl, phenyl, tolyl, xylyl, naphthyl, phenylalkyl and the like that may have various acceptable substituents, such as alkyl, alkenyl, cycloalkyl, aryl, alkoxy, ester, acyloxy, a halogen atom, nitro, and cyano. When $R^5$ and $R^6$ form a ring, $R^5$ and $R^6$ may be selected to form a carbon-bonding chain on which any of various acceptable substituents such as alkyl, alkenyl, cycloalkyl, aryl, alkoxy, ester, acyloxy, a halogen atom, nitro, and cyano is present. Although $R^5$ and $R^6$ are not particularly limited, $R^7$ is preferably hydrogen. $R^8$, $R^{10}$, and $R^{11}$ are preferably hydrogen and $R^9$ is preferably hydrogen or an alkoxy group (e.g., a methoxy group or an ethoxy group).

Examples of the anionic group represented by X and Y in general formula (1) include fluoride anions, chloride anions, bromide anions, iodide anions, acetoxy anions, benzoyloxy anions, (2,6-dihydroxybenzoyl)oxy anions, (2,5-dihydroxybenzoyl)oxy anions, (3-aminobenzoyl)oxy anions, (2,6-methoxybenzoyl)oxy anions, (2,4,6-triisopropylbenzoyl)oxy anions, 1-naphthalene carboxylate anions, 2-naphthalene carboxylate anions, trifluoroacetoxy anions, trifluoromethanesulfoxy anions, tetrahydroborate anions, tetrafluoroborate anions, and the like. Among these, halogen anions such as fluoride anions, chloride anions, bromide anions, and iodide anions are preferred.

The process for producing a tert-alkyl alcohol according to the present invention is a process of hydrogenating a tert-alkyl ketone under pressurized hydrogen in the presence of any one of the ruthenium complexes described above and a base to obtain a corresponding tert-alkyl alcohol.

The ruthenium complex is preferably used such that the molar ratio S/C of the tert-alkyl ketone (S), which is a substrate, to the ruthenium complex (C) is in the range of 10 to 5000000, and more preferably 100 to 100000. It is preferable that a ruthenium complex have an optically active 1,1'-binaphthyl group as W since a corresponding optically active tert-alkyl alcohol can be yielded from the tert-alkyl ketone. Furthermore, the molar ratio of the base to the ruthenium complex is preferably in the range of 0.5 to 500, more preferably 40 to 400. Examples of types of base include hydroxides of alkali metals such as potassium hydroxide and sodium hydroxide and alkoxides of alkali metals such as potassium methoxide and potassium tert-butoxide.

Any suitable solvent may be used as the reaction solvent. Alcohol solvents, such as methanol, ethanol, 2-propanol, butanol, benzyl alcohol, and the like, are preferred, and ethanol is particularly preferred among these.

Although a hydrogen pressure of 0.5 atm is sufficient, from the economical viewpoint, the hydrogen pressure is preferably in the range of 1 to 200 atm, and more preferably 3 to 50 atm. The reaction temperature is preferably in the range of 0 to 100° C. and more preferably near room temperature in the range of 15 to 45° C. The reaction time will vary with reaction substrate concentration, temperature, pressure, and other reaction conditions, and the reaction takes a few minutes to a few days to complete. With respect to the form of hydrogenation reaction, either a batch process or a continuous process may be employed The tert-alkyl ketones that can be used in the process for producing the tert-alkyl alcohol of the present invention are not particularly limited. Examples thereof include ketones having three alkyl groups which are the same or different at the α-position (including ketones having two or more of the alkyl groups bonded to form a ring), cyclic ketones having two alkyl groups which are the same or different at the α-position, esters having two alkyl groups which are the same or different at the α-position and a carbonyl carbon at the β-position (e.g., α-dialkyl-β-ketoester). When β-dialkyl-β-ketoester is used, the carbon-oxygen double bond at the β-position is hydrogenated to yield α-dialkyl-β-hydroxy ester.

EXAMPLES

Example 1

Synthesis of Ruthenium Complex

A ruthenium complex (R)-1 (RuCl$_2$-[(R)-tolbinap](pica)) shown in chemical formula 2 below was synthesized as follows. First, 105.5 mg (0.21 mmol) [RuCl$_2$($\eta^6$-benzene)]$_2$ (Aldrich Chemical), 2 equivalents (R)-TolBINAP (286.0 mg, 0.42 mmol) (AZmax Co.), and 5.0 mL DMF were placed in a 10 mL Schlenk flask under argon atmosphere to prepare a solution. After argon was passed through the solution for five minutes, the solution was heated at 100° C. for 10 minutes. The solvent was then removed under vacuum, 45.4 mg (0.42 mmol) of 2-picolylamine (PICA) (Tokyo Chemical Industry Co., Ltd.) was added thereto along with 3.0 mL of methylene chloride, and the resulting solution was stirred for 2 hours. By decreasing the volume to about 0.5 mL and then adding hexane (2 mL), yellow precipitates were formed. The supernatant was removed by filtration, and the resulting powder was vacuum-dried to yield a ruthenium complex (R)-1 in 86% yield (322.0 mg). The ruthenium complex (R)-1 was used in the hydrogenation reaction described below without purification. The melting point was >150° C. (decomposition point).

The ruthenium complex (R)-1 was obtained as a diastereomer mixture. By heating this mixture at 80° C. for 30 minutes in toluene, the content of the main diastereomer increased to >90% in terms of relative integral. The spectrum data of the ruthenium complex (R)-1 was as follows: $^1$HNMR (400 MHz, C$_6$D$_6$) δ1.78 (s, 3, CH$_3$), 1.90 (s, 3, CH$_3$), 2.28 (s, 3, CH$_3$), 2.33 (s, 3, CH$_3$), 2.86 (br s, 1, NHH), 3.22 (br s, 1, NHH), 3.95 (br s, 1, CHH), 4.93 (br s, 1, CHH), 6.19-8.36 (m, 32, aromatics); $^{31}$PNMR (161.7 MHz, C$_6$D$_6$) δ44.74 (d, J =35.6 Hz), 41.93 (d, J=35.6 Hz). However, the reaction rate and the enantioselectivity of the hydrogenation reaction of the ketone described below are independent of the initial diastereomer mixture.

A ruthenium complex (S)-1 (RuCl$_2$[(S)-tolbinap](pica)) shown in chemical formula 2 below was synthesized in the same manner by using (S)-TolBINAP instead of (R)-TolBINAP.

Chemical formula (2)

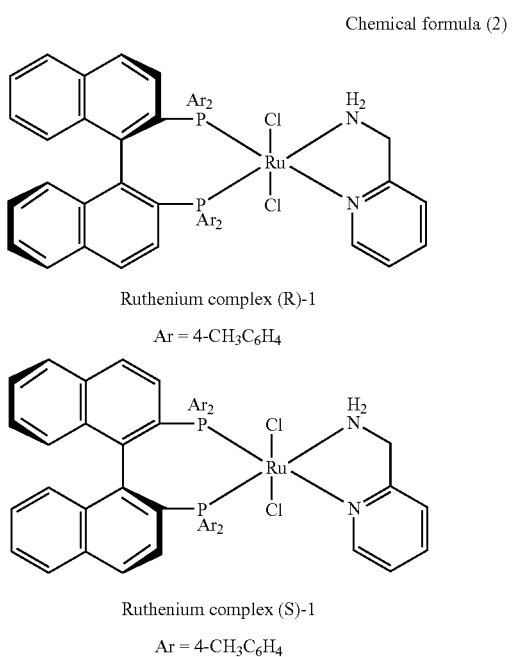

Ruthenium complex (R)-1

Ar = 4-CH$_3$C$_6$H$_4$

Ruthenium complex (S)-1

Ar = 4-CH$_3$C$_6$H$_4$

Examples 2 to 15

Hydrogenation Reaction of tert-alkyl Ketones

Various tert-alkyl ketones shown in Tables 1 and 2 as Examples 2 to 15 were subjected to hydrogenation reaction to yield corresponding tert-alkyl alcohols in high yield at high enantioselectivities (see reaction schemes of chemical formulae 3 to 7 below). A representative process of hydrogenation reaction is presented below. That is, into a 100 mL glass autoclave (containing a magnetic stirrer bar) dried at 120° C. in an oven in advance, a ruthenium complex (S)-1 (2.5 mg, 2.6 μmol) accurately weighed and solid KOC(CH$_3$)$_3$ were placed. After the autoclave was put under a high vacuum for at least five minutes, argon was introduced. Freshly distilled ethanol (6.0 mL) and a reaction substrate, tert-alkyl ketone were degassed by passing argon through the solution and then placed in an autoclave under argon atmosphere. The autoclave was connected to a hydrogen bottle, and the operation of filling the interior of the autoclave with 8 atm hydrogen and releasing it until atmospheric pressure was conducted several times. Then the hydrogen pressure was set to a target level. Hydrogenation reaction was conducted by vigorously stirring the reaction solution at 25° C. while monitoring the hydrogen consumption. Upon completion of reaction, a small quantity of crude product was analyzed with Chiral GC (column: CP-Chirasil-DEK CB, Chrompak Ltd.) to determine the conversion rate and enantiomeric excess. The products were either chromatographically purified or isolated by distillation. All the products were identified by at least $^1$HNMR and $^{13}$CNMR and their absolute configurations were determined from specific rotation or by circular dichroic spectroscopy. Note that the hydrogenation reaction of each example was conducted according to the representative process described above, and the molar ratio (S/C) of tert-alkyl ketone (substrate) to the ruthenium complex (C), the molar ratio (Base/C) of the base to the ruthenium complex, the hydrogen pressure, and the reaction time were set as shown in Tables 1 and 2.

TABLE 1

| | Ketone | Ruthenium complex | S/C | Base/C | Hydrogen pressure (atm) | Reaction time (hr) | Alcohol %, Yield | % ee | Form |
|---|---|---|---|---|---|---|---|---|---|
| Example 2 | 2a | (S)-1 | 2000 | 50 | 5 | 5 | 100 | 97 | S |
| Example 3 | 2a | (S)-1 | 100000 | 353 | 20 | 24 | 100 | 98 | S |
| Example 4 | 2b | (R)-1 | 2300 | 190 | 5 | 5 | 100 | 97 | R |
| Example 5 | 2c | (S)-1 | 2000 | 50 | 5 | 5 | 100 | 97 | R |
| Example 6 | 2d | (S)-1 | 2400 | 283 | 8 | 5 | 99 | 97 | Not assigned |
| Example 7 | 2e | (S)-1 | 2100 | 142 | 8 | 5 | 100 | 98 | Not assigned |
| Example 8 | 2f | (S)-1 | 2050 | 49 | 5 | 5 | 100 | 97 | Not assigned |
| Example 9 | 2g | (R)-1 | 2040 | 160 | 8 | 5 | 99.6 | 98 | R |

TABLE 2

| | Ketone | Form of Catalyst | S/C | Base/C | Hydrogen pressure (atm) | Reaction time (hr) | Alcohol %, Yield | % ee | Form |
|---|---|---|---|---|---|---|---|---|---|
| Example 10 | 4a | S | 2000 | 52 | 5 | 5 | 100 | 97 | S |
| Example 11 | 4b | S | 2000 | 47 | 5 | 5 | 100 | 82 | S |
| Example 12 | 6 | S | 2000 | 60 | 5 | 5 | 100 | 98 | S |
| Example 13 | 7 | S | 2250 | 122 | 8 | 5 | 95 | 84 | S |
| Example 14 | 8a | R | 2050 | 112 | 8 | 20 | 99.6 | 90 | S |
| Example 15 | 8b | R | 2400 | 142 | 8 | 5 | 100 | 98 | S |

[Examples 2 to 9]

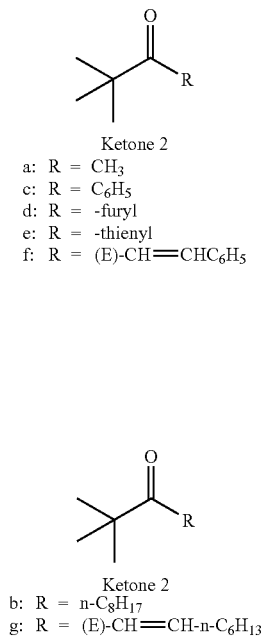

Chemical formula 3

[Examples 10 and 11]

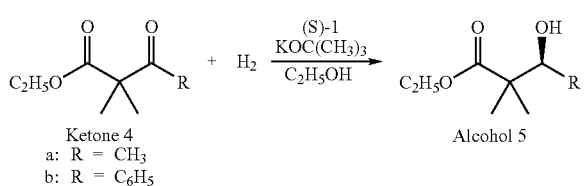

[Example 12]

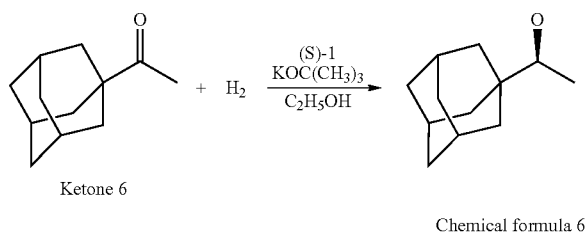

[Example 13]

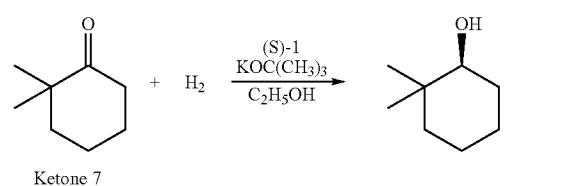

[Examples 14 and 15]

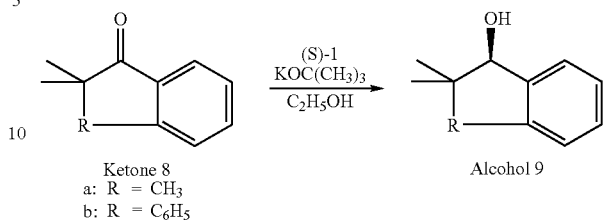

Chemical formula 7

As shown in Tables 1 and 2, the novel ruthenium complexes, (R)-1 and (S)-1 allow asymmetric hydrogenation reaction of sterically bulky tert-alkyl ketones to proceed when used with strong bases to give corresponding chiral tert-alkyl alcohols. tert-Alkyl ketones may be aliphatic, aromatic, cyclic, or acyclic. The hydrogenation reaction smoothly proceeds under mild conditions at S/C of 2000 to 100000.

It should be noted that pinacolone 2a used in Examples 2 and 3 were purchased from Aldrich Chemical. Ketone 2b (2,2-dimethyl-3-undecanone) used in Example 4 was obtained by reacting 1-nonanal with tert-butyl magnesium chloride to synthesize 2,2-dimethyl-3-undecanol and oxidizing the resultant 2,2-dimethyl-3-undecanol with bichromic acid. Ketone 2c (pivalophenone(tert-butylphenyl ketone)) used in Example 5 was purchased from Aldrich Chemical. Ketone 2d (2,2-dimethyl-1-(2-furyl)-1-propanone) used in Example 6 was obtained by reacting 2-furaldehyde with tert-butyl magnesium chloride to yield 2,2-dimethyl-1-(2-furyl)-1-propanol and then oxidizing the resultant 2,2-dimethyl-1-(2-furyl)-1-propanol with N-methylmorpholine-N-oxide in the presence of a catalyst, TPAP (tetrapropylammonium perruthenate). Ketone 2e (2,2-dimethyl-1-(2-thienyl)-1-propanone) used in Example 7 was obtained by reacting thiophene with pivaloyl chloride in the presence of aluminum chloride. Ketone 2f (4,4-dimethyl-1-phenyl-3-pentenone) used in Example 8 was synthesized by a previously reported process (Org. Syn. Coll. Vol I, 81-82). Ketone 2g ((E)-2,2-dimethyl-4-undecen-3-one) used in Example 9 was obtained as a mixture with a ratio E/Z of 5:1 by reacting 1-bromo-3,3-dimethyl-2-butanone, which was obtained by bromination of pinacolone, with triphenylphosphine, treating the resultant product with sodium hydroxide to yield phosphorus ylide, and then reacting the resultant phosphorus ylide with 1-heptanal. Ketone 4a (ethyl 2,2-dimethyl-3-oxobutanoate) used in Example 10 was synthesized by a previously reported process (J. Am. Chem. Soc. 1988, vol 110, pp. 1539-1546). Ketone 4b (ethyl 2,2-dimethyl-3-oxo-3-phenyl propionate) used in Example 11 was also synthesized by a previously reported process (J. Chem. Soc., Perkin Trans. I 1986, pp. 1139-1143). Ketone 6 (adamantyl methyl ketone) used in Example 12 and ketone 7 (2,2-dimethylcyclohexanone) used in Example 13 were purchased from Aldrich Chemical. Ketone 8a (2,2-dimethyl-1-indanone) used in Example 14 and ketone 8b (2,2-dimethyl-1-tetralone) used in Example 15 were synthesized by previously reported processes (J. Am. Chem. Soc. 1975, vol. 97, pp. 4667-4672).

Alcohols 3a obtained in Examples 2 and Example 3 showed $[\alpha]^{22}_D=+5.8°$ and $[\alpha]^{22}_D=+7.8°$, respectively. Since the literature value of the S-form was $[\alpha]^{22}_D=+8.1°$, they were identified as S-form. Alcohol 3b obtained in Example 4 showed $[\alpha]^{25}{}_D$=+29.1° and was identified as R-form since the specific rotation of the S-form synthesized by a known process was $[\alpha]^{25}{}_D$=−27.3°. Alcohol 3d obtained in Example 5 showed $[\alpha]^{25}{}_D$=+24.3°. Since the literature value of the R-form was $[\alpha]_D$=+25.9°, alcohol 3d was identified as R-form. Absolute configurations of Examples 6 to 8 were not assigned. Alcohol 3 g obtained in Example 9 was identified as S-form since the specific rotation of alcohol 3b after reduction of olefin was $[\alpha]^{25}{}_D$=−28.5° and the value of the preparation of the S-form was $[\alpha]^{25}{}_D$=−27.3°. Alcohol 5a obtained in Example 10 showed $[\alpha]^{25}{}_D$=+9.8° and was determined as S-form since the literature value of the S-form was $[\alpha]_D$=+6.98°. Alcohol 5b obtained in Example 11 was identified as S-form since the specific rotation as 2,2-dimethyl-3-hydroxy-3-phenyl propanoic acid was $[\alpha]^{25}{}_D$=+6.2° and the literature value of the R-form was $[\alpha]^{25}{}_D$=−4.7°. The alcohol obtained in Example 12 was identified as S-form since the specific rotation as an acetate derivative was $[\alpha]^{25}{}_D$=−11.3° and the literature value of the R-form was $[\alpha]^{25}{}_D$=+18.1°. The alcohol obtained in Example 13 was identified as S-form since the specific rotation as 3,5-dinitro benzoate derivative was $[\alpha]_D$=−35.6° and the literature value of the S-form was $[\alpha]^{20}{}_D$=−42.5°. Alcohol 9a obtained in Example 14 showed $[\alpha]^{20}{}_D$=+24.4° and was identified as S-form since the literature value of the S-form was $[\alpha]^{22}{}_D$=+29.0°. Alcohol 9b obtained in Example 15 showed $[\alpha]^{24}{}_D$=+18.7° and was identified as S-form since the literature value of the R-form was $[\alpha]^{22}{}_D$=−23.5°.

The present invention claims priority to Japanese Patent Application No. 2004-309919 filed on Oct. 25, 2004, the entire contents of which are incorporated herein by reference.

INDUSTRIAL APPLICABILITY

The present invention is applicable mainly in the pharmaceutical and chemical industries. For example, the present invention can be used in synthesis of various optically active tert-alkyl alcohols useful as intermediates for medicines or agricultural chemicals.

The invention claimed is:

1. A process for producing a tert-alkyl alcohol, comprising hydrogenating a tert-alkyl ketone under pressurized hydrogen in the presence of a ruthenium complex represented by general formula (1):

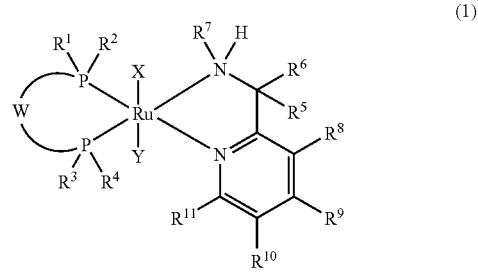

wherein W is a substituted or unsubstituted bonding chain; $R^1$ to $R^4$ may be the same or different and each represent a substituted or unsubstituted hydrocarbon group; $R^5$ to $R^{11}$ may be the same or different and each represent hydrogen or a substituted or unsubstituted hydrocarbon group; X and Y represent the same or different anionic groups; and each ligand of Ru may take any configuration.

2. A process for producing a tert-alkyl alcohol according to claim 1,
wherein W is optically active, and the corresponding tert-alkyl alcohol is optically active.

3. The process for producing the tert-alkyl alcohol according to claim 1, wherein the hydrogenation is conducted in an ethanol solvent.

4. The process for producing the tert-alkyl alcohol according to claim 1, wherein a molar ratio S/C of the tert-alkyl ketone to the ruthenium complex is 100 to 100000.

5. The process for producing the tert-alkyl alcohol according to claim 1, wherein the tert-alkyl ketone is a ketone having three alkyl groups, which are the same or different, at the α-position, at least two of which may be bonded to form a ring.

6. The process for producing the tert-alkyl alcohol according to claim 1, wherein the tert-alkyl ketone is a cyclic ketone having two alkyl groups, which are the same or different, at the α-position.

7. The process for producing the tert-alkyl alcohol according to claim 1, wherein the tert-alkyl ketone is α-dialkyl-β-ketoester and the corresponding tert-alkyl alcohol is α-dialkyl-β-hydroxyester in which carbonyl at the β-position is hydrogenated.

* * * * *